United States Patent
Fauconet et al.

(10) Patent No.: US 6,352,619 B1
(45) Date of Patent: Mar. 5, 2002

(54) METHOD FOR PURIFYING ACRYLIC ACID

(75) Inventors: Michel Fauconet, Valmont; Francis Augustin, Lindre Basse; Marc Esch, Freyming Merlebach, all of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/254,874

(22) PCT Filed: Sep. 12, 1997

(86) PCT No.: PCT/FR97/01613

§ 371 Date: Apr. 14, 1999

§ 102(e) Date: Apr. 14, 1999

(87) PCT Pub. No.: WO98/11048

PCT Pub. Date: Mar. 19, 1998

(30) Foreign Application Priority Data

Sep. 16, 1996 (FR) ............................................. 96 11269

(51) Int. Cl.⁷ ........................... B01D 3/34; C07C 51/44; C07C 51/50; C07C 51/487; C07C 57/04
(52) U.S. Cl. ............... 203/8; 203/59; 203/29; 203/71; 203/DIG. 21; 562/600
(58) Field of Search .................... 203/9, 8, 6, DIG. 21, 203/29, 38, 71, 59; 562/600

(56) References Cited

U.S. PATENT DOCUMENTS

| 3,725,208 A | | 4/1973 | Maezawa et al. ............... 203/8 |
| 3,988,213 A | * | 10/1976 | Yoshida et al. ...... 203/DIG. 21 |
| 4,600,898 A | | 8/1983 | Frank et al. ................. 562/599 |
| 4,828,652 A | * | 5/1989 | Schropp ..................... 562/600 |
| 5,571,386 A | * | 11/1996 | Bauer, Jr. et al. ............. 203/38 |
| 5,605,992 A | * | 2/1997 | Urashima et al. ........... 526/217 |
| 5,746,892 A | * | 5/1998 | Bauer, Jr. et al. .... 203/DIG. 21 |
| 5,759,358 A | * | 6/1998 | Bauer, Jr. et al. ........... 562/600 |
| 5,897,749 A | * | 4/1999 | Kroker et al. ....... 203/DIG. 21 |
| 5,961,790 A | * | 10/1999 | Herbst et al. ................ 562/600 |

FOREIGN PATENT DOCUMENTS

| EP | 085898 | 4/1983 |
| WO | 9607631 | 3/1996 |

* cited by examiner

*Primary Examiner*—Virginia Manoharan
(74) *Attorney, Agent, or Firm*—Millen, White, Zelano & Branigan, P.C.

(57) ABSTRACT

Process for purifying acrylic acid in order to remove the polymer-type impurities in those places in the distillation columns in which they have a tendency to accumulate, and more particularly a process directed towards removing the polymeric impurities which are formed during a step for removing the aldehyde impurities from acrylic acid, according to which step the medium containing the acrylic acid to be purified is distilled by adding to this medium at least one amino compound of hydrazine type and by flushing away, at the foot of the distillation column, the heavy compounds formed by the said hydrazine-type amino compound(s) with the impurities.

According to the invention, the acrylic acid to be purified is also distilled in the presence of at least one compound from the class of nonionic surface agents and of at least one polymerization inhibitor. Polysaccharide ethers and acetates, in particular ethers derived from cellulose or starch, may be mentioned as nonionic surface agents.

27 Claims, No Drawings

METHOD FOR PURIFYING ACRYLIC ACID

FIELD OF THE INVENTION

The present invention relates to an improvement to the standard process for purifying acrylic acid, in particular to steps directed towards obtaining a monomer of very high purity, intended for the manufacture of technical-grade polymers of very high molecular masses.

BACKGROUND OF THE INVENTION

The main route for the synthesis of acrylic acid which is used industrially today involves a catalytic oxidation of propylene, generating acrolein as an intermediate. This reaction also produces side impurities, among which are carbonyl impurities such as aldehydes, for instance furfuraldehyde (or furfural) and benzaldehyde, in addition to the acrolein. These compounds are a great nuisance, even at extremely low contents, since they make it impossible to manufacture polymers of high molecular masses, which are desired in many applications.

The present invention thus relates to a process for purifying acrylic acid, and more particularly to a step of this process in which the carbonyl impurities present in the general flow (aldehydes and ketones) are removed by addition of a compound such as hydrazine during a distillation step, the hydrazine-type compound forming, with these impurities, heavy compounds which are flushed away at the foot of the distillation column.

The standard processes for purifying acrylic acid involve successive distillation steps directed towards removing the light impurities (water, acrolein, acetic acid, etc.) and the heavy impurities (maleic acid, acryloxypropionic acid, etc.) which are formed during the reaction or purification steps.

During these steps of purification by distillation, it often occurs that polymers are formed, under the effect of heat, this occurring even under operating conditions directed, for example by carrying out the distillations under reduced pressure, towards reducing the temperature of the flows rich in polymerizable monomers. In the case of acrylic acid, since the polymer is insoluble in the monomer, it precipitates in the medium and gives rise to deposits on certain parts of the plant, for instance the exchangers.

The formation of these solid deposits is a particular nuisance, since they form an insulating layer which reduces the heat exchange, the consequence of which is to cause an increase in the heating in order to maintain a constant temperature in the boiling vessel, thereby entailing an aggravation of the polymerization phenomenon. In this case, one is limited to rapidly stopping the distillation in order to carry out a difficult and expensive cleaning of the plant.

It is well known that the distillation of acrylic monomers, which readily polymerize under the action of radicals formed, for example, by the effect of heat, necessitates the use of polymerization inhibitors, particularly during the distillation steps. The compounds typically used for this purpose are, for example, phenolic derivatives, for instance hydroquinone or hydroquinone methyl ether; phenothiazine and its derivatives; derivatives of the thiocarbamate family; compounds containing a nitroso group; quinones; or alternatively aromatic amines.

Despite the use of these polymerization inhibitors, polymers can gradually accumulate, more or less quickly depending on the purification step and the operating conditions of the equipment through which the monomer-rich flow passes, in the form of interfering deposits.

These problems are particularly acute during a final step of purification of the acrylic acid.

With the aim of obtaining an acrylic acid of very high quality in terms of purity, the removal of all of these impurities, down to extremely low contents, is not economically achievable by means of a simple separation by distillation. In particular, on account of their volatility which is close to that of acrylic acid, the abovementioned carbonyl impurities cannot be removed efficiently, down to the extremely low contents targeted, by a single distillation operation.

In order to remove the aldehyde impurities, American patent U.S. Pat. No. 3,725,208 describes a chemical treatment which consists in adding amines to the impure mixture and then in distilling the mixture obtained. The amine family is particularly suitable for achieving this aim, since these compounds have the particular feature of forming, with aldehydes, heavy compounds which can readily be separated from the acrylic acid at the foot of the distillation column. Among the reagents which offer the best efficacy, the ones described in particular are those which form part of the hydrazine family, such as glycine (Japanese patent No. J 7,500,014) or hydrazine itself or its derivatives (American patent U.S. Pat. No. 3,725,208 and Japanese patent J 7,430, 312) or alternatively aminoguanidine (European patent EP-B-270,999) or salts thereof.

The chemical treatments which are described all have the drawback of generating water during the reaction of the aldehyde with the amino reagent. The presence of this impurity in the acrylic acid is also harmful with respect to the reactivity of the monomer in its most technical applications. For this reason, it may be particularly advantageous to carry out this chemical treatment during a step of distillation directed towards removing the water and the light head-fraction compounds, before the step of distillation of the acrylic acid which is intended to separate out the heavy compounds, as is described in Japanese patent J 7,495,920.

A second major drawback of the chemical treatments for the removal of aldehydes with amines is that they entail a significant reduction in the stability of the medium. The amine function of these compounds gives them the property of reacting not only with aldehydes, but also with the acrylic acid itself, to form salts by reaction with the carboxylic part of the molecule, or Michael addition compounds by reaction of the amine with the acrylic double bond.

The reaction products of amines with acrylic acid result in an exacerbated sensitivity of the reaction medium with respect to polymerization. Despite the use of inhibitors conventionally used for the distillation of this monomer, when this treatment is carried out specifically in this distillation, in order to remove, at the foot of the column, the heavy addition compounds of the aldehydes with the amine, polymer deposits are observed, particularly on the hot wall of the boiling vessel.

The formation of these solid deposits rapidly leads to problems of blockage of the pipes or a change in the heat exchanges described above, making it necessary to stop the plant for cleaning.

In order to reduce these harmful effects, European patent application EP-A1-0,648,732 claims the use of an organic sulphonic acid during the treatment for the removal of the aldehydes with an amine such as hydrazine or aminoguanidine. This improvement has several major drawbacks. Firstly, the sulphonic acids described are corrosive and require the use of expensive equipment for those parts of the plant which come into contact with them. Moreover, large amounts of additives are used, since they must be used in an excessive molar ratio with respect to the amino compound, thus making the treatment expensive.

With the same aim of avoiding the deposition of polymers in this step of the process for purifying acrylic acid, British patent application GB-A-2,285,046 describes an improvement which consists in carrying out the treatment for the removal of the impurities with hydrazines, during a distillation, by adding a copper dithiocarbamate compound. The compounds of this metal thiocarbamate family are well known as polymerization inhibitors for acrylic acid and other acrylic and methacrylic monomers. Unfortunately, they have the drawback of entailing, in the undistillable heavy by-products of the plant, metallic residues which make them difficult to be removed. The reason for this is that these residues can cause the encrustation of the incineration ovens, thus necessitating a high cost for their removal.

In general, the addition of polymerization inhibitors is not sufficient for totally preventing the formation of polymers and solid materials during the chemical treatment for removing the carbonyl impurities from acrylic acid.

SUMMARY OF THE INVENTION

This invention provides the novel idea of reducing the drawbacks due to the solid deposits during the steps for purifying acrylic acid, and in particular during this critical step of distillation in the presence of hydrazine derivatives, by preventing them from attaching to the sensitive walls of the distillation device, by means of the use of surface agents, also known as surfactants. These products have the particular feature in common of having a hydrophilic part and a hydrophobic part in their structure. This structure gives them properties which are mainly exploited in aqueous media. Mention is made, for example, of: detergency, in which the molecule is used to facilitate the removal of soiling and dirt in water; dispersion, in order to increase the stability of the suspension of small solid particles in an aqueous liquid; the emulsification property, in which the surface agent facilitates the dispersion, in the form of fine droplets, of a hydrophobic liquid in water, or, on the contrary, of water in a hydrophobic liquid; the foaming or, on the contrary, antifoaming property, in which the compound brings about or prevents the formation of foams; or alternatively solubilization, in which the product is used to increase the apparent solubility in water of relatively insoluble substances.

A large number of products with a property of this type are known. They are commonly classified, depending on their structure, as anionic, cationic, amphoteric and nonionic surface agents.

It has now been discovered, surprisingly, that the addition of very small amounts of compounds of the class of nonionic surface agents, and more particularly within this class, the family of polysaccharide ethers, alone or in combination, in the presence of polymerization inhibitors, significantly reduces the amount of polymer deposits, particularly in the reboilers of the acrylic acid distillation columns, and mainly in the exchangers located at the foot of the column or in the column feed, during an acrylic acid distillation step carried out in an essentially anhydrous medium. This improvement is particularly exploited when the acrylic acid distillation is carried out in the presence of compounds such as hydrazine, in order to remove the aldehyde impurities. Thus, in accordance with the process of the present invention, the distillation time is increased significantly, thus greatly reducing the encrustation caused by the deposits. In addition, when the invention is carried out in the context of a purification process using an amino compound directed towards removing the aldehyde impurities from the acrylic acid, the small deposits, which are accumulated over a much longer period of time than under the conditions known in the prior art, are much more readily removed than those of this prior art, since a simple operation of washing with water makes it possible to clean the encrusted equipment effectively.

A subject of the present invention is thus a process for purifying acrylic acid which is directed towards removing the polymer-type impurities in those places in the distillation columns in which they have a tendency to accumulate, and more particularly a process directed towards removing the polymeric impurities which are formed during a step for removing the aldehyde impurities from acrylic acid, according to which step the medium containing the acrylic acid to be purified is distilled by adding to the said medium at least one amino compound of hydrazine type and by flushing away, at the foot of the distillation column, the heavy compounds formed by the said hydrazine-type amino compound(s) with the said impurities, characterized in that the distillation of the acrylic acid to be purified is also carried out in the presence of at least one compound of the nonionic surface agent category and of at least one polymerization inhibitor.

The nonionic surface agents which are useful in accordance with the present invention are, in particular:

compounds of the polysaccharide ether and acetate family, preferably the ethers, and in particular those which are derived from cellulose or from starch, such as those represented by formula (I):

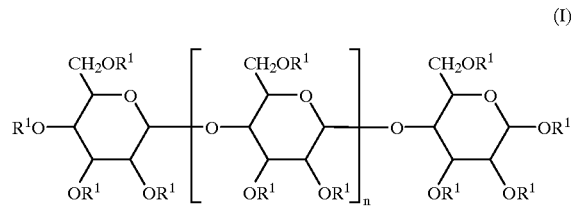

(I)

in which:
the groups $R^1$ independently represent H; a $C_1$–$C_4$ alkyl group; $CH_3CO$—,

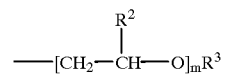

with $R^2$=H, $CH_3$ or $C_2H_5$, m=integer from 1 to 20 and $R^3$=H or $C_1$–$C_4$ alkyl or $CH_3CO$—; and
n is an integer greater than 1, representing the number of chain units in a polymer chain;

ethylene glycol and propylene glycol derivatives or ethers thereof, represented by formula (II):

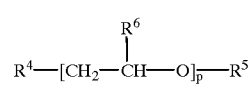

(II)

in which:
$R^4$ and $R^5$ each independently represent HO— or $R^7O$— or $R^7$—$C_6H_4O$— with $R^7$ representing a $C_1$–$C_{20}$ alkyl group;

$R^6$ represents H or $CH_3$; and p is an integer from 3 to 20;

glycol ester derivatives, represented by formula (III):

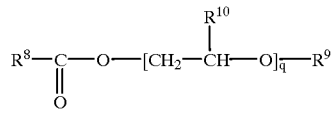
(III)

in which:

$R^8$ represents a $C_8$–$C_{20}$ alkyl group;

$R^9$ represents H or a $C_8$–$C_{20}$ alkyl group;

$R^{10}$ represents H or $CH_3$;

q is an integer from 1 to 20;

glyceryl ester derivatives, represented by formula (IV):

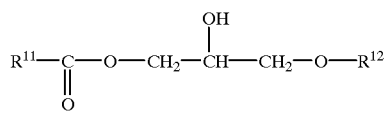
(IV)

in which:

$R^{11}$ represents a $C_8$–$C_{20}$ alkyl group; and $R^{12}$ represents H or

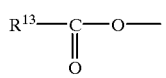

$R^{13}$ representing a $C_8$–$C_{20}$ alkyl group;

carboxylic amide derivatives, represented by formula (V):

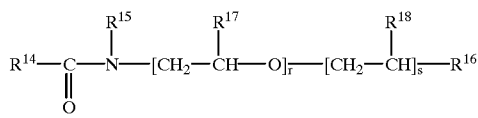
(V)

in which:

$R^{14}$ represents a $C_8$–$C_{20}$ alkyl group;

$R^{15}$ represents H or

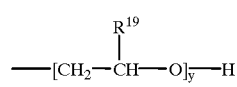

with $R^{19}$ representing H or $CH_3$ and y being an integer from 1 to 5;

$R^{16}$ represents H or

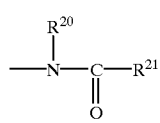

in which $R^{20}$ represents H or

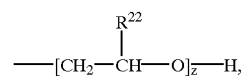

with $R^{22}$ representing H or $CH_3$ and z is an integer from 1 to 5, and $R^{21}$ is a $C_8$–$C_{20}$ alkyl;

$R^{17}$ and $R^{18}$ each independently represent H or $CH_3$;

r being equal to 0 or being an integer from 1 to 20; and s being equal to 0 or 1.

The compounds of formula (I) are preferably used alone or as a mixture with the surface agents described of formulae (II) to (V) above.

The nonionic surface agent compound(s) can be sent into the flow containing the acrylic acid to be purified, alone (when they are liquid products) or in solution or suspension in a solvent. Preferably, when they are solid compounds, they are first dissolved or suspended in a solvent, such as, for example, acrylic acid, acetic acid, propionic acid, maleic acid, maleic anhydride or water. Even more advantageously, the solid nonionic surface agent compounds are added in solution in a medium containing acrylic acid, for instance the solution rich in polymerization inhibitors which is used to inject these inhibitors into the top or into the feed of the distillation columns.

Generally, the nonionic surface agent compound(s) is(are) added in a proportion of 10–10,000 ppm, preferably 10–1000 ppm, relative to the medium containing the acrylic acid to be purified.

At least one polymerization inhibitor is also added to the medium containing the acrylic acid to be purified, in a proportion in particular of 5–10,000 ppm, preferably of 10–5000 ppm, relative to the medium containing the acrylic acid to be purified, this inhibitor being chosen in particular from phenolic derivatives, for instance hydroquinone and its derivatives, such as hydroquinone methyl ether; phenothiazine and its derivatives, such as methylene blue; metal thiocarbamates, such as copper dibutyldithiocarbamate; compounds containing nitroso groups, such as N-nitrosophenylhydroxylamine; quinones such as benzoquinone; para-phenylenediamine derivatives represented by the general formula (VI):

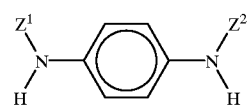
(VI)

in which $Z^1$ and $Z^2$ each independently represent an alkyl, aryl, alkylaryl or arylalkyl radical.

In the context of a process using a hydrazine-type amino compound, which is directed towards removing the aldehyde impurities present in acrylic acid, the hydrazine-type amino compound is chosen from hydrazine; hydrazine hydrate; alkylhydrazines such as cyclohexylhydrazine or hexadecylhydrazine; phenylhydrazine; 2-naphthylhydrazine; tolylhydrazine; p-nitrophenylhydrazine; 2,4-dinitrophenyl-hydrazine; glycine; guanidine; aminoguanidine; and salts thereof. The hydrazine-type amino compound(s) is(are) generally added in a proportion of 10–10,000 ppm, preferably of 100–5000 ppm, relative to the medium containing the acrylic acid to be purified.

It moreover turns out that, in accordance with the present invention, the hydrazine-type amino compound(s) can advantageously be added in an amount such that the molar ratio: hydrazine-type compound(s)/sum of the aldehydes present in the feed, is 0.5/1–10/1, in particular 1/1–5/1.

The process according to the present invention can be carried out in batchwise mode, or alternatively in continuous mode, for example in the flow of acrylic acid to be purified feeding the monomer distillation column.

Even more advantageously, it is possible to carry out the treatment, which generates water during the reaction of the hydrazine-type compounds with the carbonyl impurities, in the flow feeding a column allowing the removal of the light impurities and the water at the top, the flow at the foot of this head-fraction-removal column then being sent as a feed for the final column which carries out the distillation of the pure acrylic acid at the top and the removal of the heavy compounds at the foot (compounds of reaction of the aldehyde impurities with the hydrazine-type components, inhibitors, nonionic surface agents, etc.). Thus, the distillation can be carried out in two successive steps:

the first step, in a first column for removal of the head fraction (C1), fed with the flow of acrylic acid to be purified and receiving the hydrazine-type amino compound(s), in order to remove, at the top of the column, the light impurities and the water generated during the reaction of the hydrazine-type compound(s) with the aldehyde impurities; and the second step, in a second distillation column (C2), fed with the flow from the foot of the said column for removal of the head fraction, in order to carry out, at the top of the column, the distillation of the pure acrylic acid, and, at the foot of the column, the removal of the heavy compounds, consisting in particular of the products of reaction of the aldehyde impurities with the hydrazine-type compounds, the polymerization inhibitor(s) and the nonionic surface agent(s), the polymerization inhibitor(s) being added to the top of the column (C1) and to the top of the column (C2), and optionally into the feed of these two columns, the nonionic surface agent compound(s) being added, alone or as mixtures, into the feed of the column (C1) and/or into the top of the columns (C1) and (C2), in which case they can be injected, for example, in a solution based on solvent or on acrylic acid containing the inhibitors, which is used to send these inhibitors to the top of the said columns.

The present invention will now be described with the aid of the Examples and Comparative Examples which follow.

EXAMPLES

In the following examples, the percentages are expressed on a weight basis relative to the mass of acrylic acid to be purified, and the following abbreviations are used:

| Inhibitors: | |
|---|---|
| PTZ | phenothiazine |
| HQ | hydroquinone |
| CB | copper di-n-butyldithiocarbamate |
| DSB-PPDA | N,N'-di-sec-butyl-para-phenylenediamine |

| Surface agents: | |
|---|---|
| NP10 | polyethoxylated (10 ethoxy) nonylphenol - product sold under the name "Tergipol NP10" (nonionic surface agent) |
| Rewopal MT65 | coconut-based polyglycol ether - tradename of a nonionic surface agent |
| DBSS | sodium dodecylbenzene sulphonate (anionic surface agent) |
| DMDNO | N,N-dimethyldodecylamine N-oxide (cationic detergent) |
| HPC KLUCEL H | hydroxypropylcellulose - tradename of a nonionic surface agent |
| MHPC xxxxx | compounds of the methyl hydroxypropyl cellulose family, characterized by viscosity of their solution at a concentration of 2% in water at 20° C., which is indicated by the extension "xxxxx" (nonionic surface agents) |
| MHEC xxxxx | compounds of the methyl hydroxyethyl cellulose family, characterized by viscosity of their solution at a concentration of 2% in water at 20° C., which is indicated by the extension "xxxxx" (nonionic surface agents) |

General Procedure for Examples 1 and 2 (reference), 3 and 4 (comparative) and 5 to 13 (of the invention)

Glass distillation equipment operating in continuous mode is used, this equipment comprising:

a distillation column C1, operating at a reduced pressure of $1.07 \times 10^4$ Pa (80 mm Hg), comprising perforated plates representing an efficacy of 6 theoretical plates, equipped:

at the foot of the column, with a boiling vessel with forced recirculation through a pump, heated by circulation of thermostatically-maintained oil in the jacket, comprising an injection of air;

at the top of the column, with a condenser, a reflux pot, a pump and a measuring system for sending some of the distillate in reflux to the top of the column;

with a pump which sends a solution of inhibitor(s) dissolved in acrylic acid into the reflux circuit of the column; and with a feed located 2/3 of the way along the column, firstly preheated by a jacketed exchanger, heated with oil, and which receives, before the exchanger, a known flow rate of hydrazine hydrate;

a distillation column, of Vigreux type, operating at a reduced pressure of $1.07 \times 10^4$ Pa (80 mm Hg), having an efficacy of 6 theoretical plates, equipped:

at the foot of the column, with a boiling vessel with forced recirculation through a pump, heated by circulation of thermostatically-maintained oil in the jacket, comprising an injection of air;

at the top of the column, with a condenser, a reflux pot, a pump and a measuring system for sending some of the distillate in reflux to the top of the column;

with a pump which sends a solution of inhibitor(s) dissolved in acrylic acid into the reflux circuit of the column; and with a feed located in the boiling vessel of the column.

The solution of inhibitor(s) dissolved in acrylic acid, sent to the top of column C1 also contains, except in the reference Examples 1 and 2, the surface agents.

5% of the flow feeding this column is distilled in column C1. 90% of the feed flow are distilled at the top of the column in column C2. The temperatures are 83 °C. at the foot of column C1 and 86° C; at the foot of column C2. The two columns operate in series, the flow at the foot of column C1 being sent continuously to the foot of column C2.

The feed flow of column C1 consists of acrylic acid containing aldehyde impurities to a level of 150–200 ppm of acrolein, 190–250 ppm of furfural and 50–100 ppm of benzaldehyde, relative to this flow.

The duration of the tests is 12 hours, at the end of which the equipment is emptied of its liquid flow, the boiling vessel at the foot of column C1 is filled with distilled water, this water is circulated at room temperature for 1 hour, using the pump which effects the recirculation in the boiling vessel during the test. The verification is made that, after this washing, no solid residue remains on the surface of the boiling vessel. The washing water is recovered in a round-bottomed flask and evaporated to dryness. The residue obtained after complete evaporation is weighed. This makes it possible to quantify the extent of the encrustation phenomenon according to the operating conditions of the various tests.

Examples 1 and 2 (reference)

These examples describe distillations carried out with treatment for the removal of the aldehydes with hydrazine hydrate, in the presence of "standard" inhibitors without addition of surface agents.

Examples 3 to 14

These examples describe distillations carried out under conditions identical to those of the Reference Examples 1 and 2, except that one or more surface agent(s) are added to the solution of inhibitors in acrylic acid sent to the top of column C1.

Examples 3 and 4

The surface agents used belong, respectively, to the group of anionic and cationic surface agents. The encrustation of the boiler of column C1 is greater than or comparable to that of the Reference Examples 1 and 2.

Examples 5 to 14

The surface agents tested belong to the group of nonionic surface agents. The results of the encrustation in the boiling vessel of column C1 are substantially better than those of the Reference and Comparative Examples 1 to 4.

The surface agents based on cellulose ether (Examples 7 to 14) achieve a marked reduction in the encrustations.

TABLE 1

| Example | 1 (reference) | 2 (reference) | 3 (comparative) | 4 (comparative) | 5 | 6 | 7 | 8 | 9 | 10 | 11 | 12 | 13 | 14 |
|---|---|---|---|---|---|---|---|---|---|---|---|---|---|---|
| Inhibitors (ppm) | | | | | | | | | | | | | | |
| sent to the top of C1 | | | | | | | | | | | | | | |
| PTZ | 800 | | | | | | | 800 | | 400 | | | | |
| HQ | 800 | | | | | | | 800 | | 400 | | | | |
| CB | | | | | | | | | | 15 | | | | |
| DSB-PPDA | | 800 | 800 | 800 | 800 | 800 | 800 | | 800 | | 800 | 800 | 800 | 800 |
| sent to the top of C2 | | | | | | | | | | | | | | |
| PTZ | 800 | | | | | | | 800 | | 400 | | | | |
| HQ | 800 | | | | | | | 800 | | 400 | | | | |
| CB | | | | | | | | | | 15 | | | | |
| DSB-PPDA | | 800 | 800 | 800 | 800 | 800 | 800 | | 800 | | 800 | 800 | 800 | 800 |
| in the feed C1 | | | | | | | | | | | | | | |
| DSB-PPDA | | | | | | | | | | 800 | | | | |
| Surface agents (sent to the top of C1) (ppm) | | | | | | | | | | | | | | |
| NP 10 | | | | | 300 | | | | | | 300 | | | |
| Rewopal MT65 | | | | | | 300 | | | | | | | | |
| DBSS | | | 300 | | | | | | | | | | | |
| DMDNO | | | | 300 | | | | | | | | | | |
| HPC | | | | | | | 100 | | | | | | | |
| KLUCEL H | | | | | | | | | | | | | | |
| MHPC 4000 | | | | | | | | 100 | 100 | 20 | 100 | | | |
| MHPC 400 | | | | | | | | | | | | 100 | | |
| MHPC 20000 | | | | | | | | | | | | | 100 | |
| MHEC 8000 | | | | | | | | | | | | | | 100 |
| Treatment conditions: | | | | | | | | | | | | | | |
| hydrazine (ppm) | 1500 | 1500 | 1500 | 1500 | 1500 | 1500 | 1500 | 1500 | 1500 | 1500 | 1500 | 1500 | 1500 | 1500 |

TABLE 1-continued

| Example | 1 (reference) | 2 (reference) | 3 (comparative) | 4 (comparative) | 5 | 6 | 7 | 8 | 9 | 10 | 11 | 12 | 13 | 14 |
|---|---|---|---|---|---|---|---|---|---|---|---|---|---|---|
| Observations | | | | | | | | | | | | | | |
| dry residue after washing with water (g) | 2.45 | 1.83 | 2.2 | (1) | 0.78 | 0.95 | 1.1 | 0.23 | 0.15 | 0.2 | 0.05 | 0.05 | 0.3 | 0.15 |
| Analyses for the top of C2 (ppm) | | | | | | | | | | | | | | |
| Acrolein | 0.2 | | 0.3 | | 0.3 | 0.25 | | <0.1 | 0.1 | 0.03 | 0.12 | 0.24 | | |
| Furfural | 0.52 | | 0.16 | | 2.1 | 0.28 | | 1.1 | 0.06 | 0.6 | 0.05 | 0.02 | | |
| Benzaldehyde | 0.75 | | 0.7 | | 5.2 | 1.75 | | 0.16 | 0.7 | 0.1 | 0.7 | 0.4 | | |

(1) extensive encrustation after a few hours of operation; test stopped due to blockage

What is claimed is:

1. In a distillation process for purifying acrylic acid contaminated with aldehyde impurities wherein polymeric impurities are formed during a step for removing the aldehyde impurities from a medium containing acrylic acid, the improvement comprising conducting the distillation of the medium containing the acrylic acid to be purified in at least one distillation column in the presence of at least one nonionic surfactant and of at least one polymerization inhibitor, said at least one nonionic surfactant being selected from the group consisting of:

compounds represented by formula (I):

$$R^1O-\underset{\underset{OR^1}{|}}{\overset{\overset{CH_2OR^1}{|}}{\bigcirc}}-O-\left[\underset{\underset{OR^1}{|}}{\overset{\overset{CH_2OR^1}{|}}{\bigcirc}}-O\right]_n-\underset{\underset{OR^1}{|}}{\overset{\overset{CH_2OR^1}{|}}{\bigcirc}}-OR^1 \quad (I)$$

in which:
the groups $R^1$ independently represent H; a $C_1$–$C_4$ alkyl group; $CH_3CO$—;

$$-[CH_2-\overset{\overset{R^2}{|}}{CH}-O]_m R^3$$

with $R^2$=H, $CH_3$ or $C_2H_5$;
m=integer from 1 to 20 and $R^3$=H or $C_1$–$C_4$ alkyl or $CH_3CO$—; and
n is an integer greater than 1, representing the number of chain units in a polymer chain;

ethylene glycol and propylene glycol derivatives or ethers thereof, represented by formula (II):

$$R^4-[CH_2-\overset{\overset{R^6}{|}}{CH}-O]_p-R^5 \quad (II)$$

in which:
$R^4$ and $R^5$ each independently represent HO— or $R^7O$— or $R^7$—$C_6H_4O$— with $R^7$ representing a $C_1$–$C_{20}$ alkyl group;
$R^6$ represents H or $CH_3$; and
p is an integer from 3 to 20;

glycol ester derivatives, represented by the formula (III):

$$R^8-\underset{\underset{O}{\|}}{C}-O-[CH_2-\overset{\overset{R^{10}}{|}}{CH}-O]_q-R^9 \quad (III)$$

in which:
$R^8$ represents a $C_8$–$C_{20}$ alkyl group;
$R^9$ represents H or a $C_8$–$C_{20}$ alkyl group;
$R^{10}$ represents H or $CH_3$;
q is an integer from 1 to 20;

glyceryl ester derivatives, represented by formula (IV)

$$R^{11}-\underset{\underset{O}{\|}}{C}-O-CH_2-\overset{\overset{OH}{|}}{CH}-CH_2-O-R^{12} \quad (IV)$$

in which:
$R^{11}$ represents a $C_8$–C20 alkyl group; and
$R^{12}$ represents H or $$R^{13}-\underset{\underset{O}{\|}}{C}-O-,$$

$R^{13}$ representing a $C_8$–$C_{20}$ alkyl group;
carboxylic amide derivatives, represented by formula (V):

$$R^{14}-\underset{\underset{O}{\|}}{C}-\overset{\overset{R^{15}}{|}}{N}-[CH_2-\overset{\overset{R^{17}}{|}}{CH}-O]_r-[CH_2-\overset{\overset{R^{18}}{|}}{CH}]_s-R^{16} \quad (V)$$

in which:
$R^{14}$ represents a $C_8$–$C_{20}$ alkyl group;
$R^{15}$ represents H or

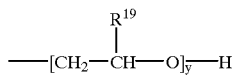

with $R^{19}$ representing H or $CH_3$ and y being an integer from 1 to 5;
$R^{16}$ represents H or

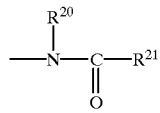

in which $R^{20}$ represents H or

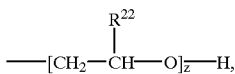

with $R^{22}$ representing H or $CH_3$ and z is an integer from 1 to 5, and $R^{21}$ is a $C_8$–$C_{20}$ alkyl;
$R^{17}$ and $R^{18}$ each independently represent H or $CH_3$;
r being equal to 0 or being an integer from 1 to 20; and
s being equal to 0 or 1.

2. A process according to claim 1, wherein the at least one nonionic surfactant is sent into a flow containing the acrylic acid, alone or in solution or suspension in a solvent, or in solution in the medium containing acrylic acid.

3. The process according to claim 2, wherein said solvent is acrylic acid, acetic acid, propionic acid, maleic anhydride or water.

4. The process according to claim 2, wherein said medium containing acrylic acid is a solution containing at least one polymerization inhibitor and wherein said solution is injected into the top or into the feed of the at least one distillation column.

5. A process according to claim 1 wherein the at least one nonionic surfactant is added in a proportion of 10–10,000 ppm, relative to the medium containing the acrylic acid to be purified.

6. A process according to claim 1 wherein the at least one polymerization inhibitor is chosen from phenolic derivatives, phenothiazine and its derivatives, metal thiocarbamates, compounds containing nitroso groups, quinones and para-phenylenediamine derivatives represented by the general formula (VI):

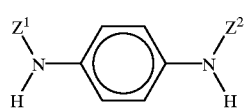

in which $Z^1$ and $Z^2$ each independently represent an alkyl, aryl, alkylaryl or arylalkyl radical.

7. The process according to claim 6, wherein the at least one polymerization inhibitor is selected from the group consisting of hydroquinone, hydroquinone methyl ether, phenothiazine, methylene blue, copper dibutyldithiocarbamate, N-nitrosophenyl hydroxylamine and benzoquinone.

8. A process according to claim 1 wherein the at least one polymerization inhibitor is added in a proportion of 5–10,000 ppm relative to the medium containing the acrylic acid to be purified.

9. A process according to claim 1, carried out in a batchwise mode, or alternatively in a continuous mode.

10. The process according to claim 9, conducted in continuous mode by feeding a flow of the medium containing acrylic acid to be purified to the at least one distillation column.

11. The process according to claim 10, comprising successive first and second distillation columns and wherein the nonionic surfactant(s) are added into the tops of the first and second columns, said surfactant(s) being injected in a solution based on solvent or on acrylic acid containing the inhibitors, said injecting being conducted to the top of said first and second distillation columns.

12. A process according to claim 1, wherein the at least one nonionic surfactant is a cellulose ether.

13. A process according to claim 12, wherein the polysaccharide is cellulose or starch.

14. A process according to claim 1, wherein said at least one nonionic surfactant is a methyl hydroxypropyl cellulose or a methyl hydroxyethyl cellulose.

15. In a process for purifying acrylic acid monomer which is directed towards removing the polymeric impurities which are formed during a step for removing aldehyde impurities from acrylic acid, said step comprising distilling a medium containing the acrylic acid to be purified in a distillation column and adding to said medium either before or during said distilling at least one hydrazine-type amino compound selected from the group consisting of hydrazine, hydrazine hydrate, alkylhydrazines, phenylhydrazine, 2-naphthylhydrazine, tolylhydrazine, p-nitrophenylhydrazine, 2,4-dinitrophenylhydrazine, glycine, guanidine, aminoguanidine, and salts thereof, removing at the foot of the distillation column, heavy compounds formed by said at least one hydrazine-type amino compound reacting with said impurities, the improvement which comprises conducting the distillation of the medium containing the acrylic acid to be purified also in the presence of at least one nonionic surfactant and of at least one polymerization inhibitor, said at least one nonionic surfactant being selected from the group consisting of:
compounds represented by formula (I):

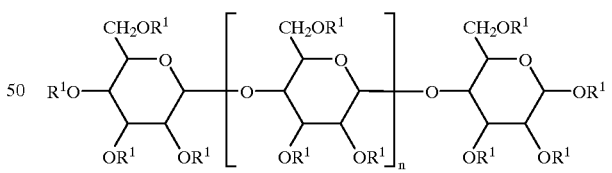

in which:
the groups $R^1$ independently represent H; a $C_1$–$C_4$ alkyl group; $CH_3CO$—;

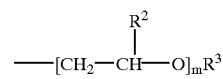

with $R^2$=H, $CH_3$ or $C_2H_5$; m=integer from 1 to 20 and $R^3$ =H or $C_1$–$C_4$ alkyl or $CH_3CO$—; and
n is an integer greater than 1, representing the number of chain units in a polymer chain;

ethylene glycol and propylene glycol derivatives or ethers thereof, represented by formula (II):

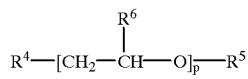
(II)

in which:
$R^4$ and $R^5$ each independently represent HO— or $R^7$—$C_6H_4O$— with $R^7$ representing a $C_1$–$C_{20}$ alkyl group;
$R^6$ represents H or $CH_3$; and
p is an integer from 3 to 20;
glycol ester derivatives, represented by the formula (III):

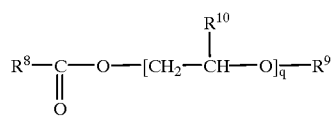
(III)

in which:
$R^8$ represents a $C_8$–$C_{20}$ alkyl group;
$R^9$ represents H or a $C_8$–$C_2$ alkyl group;
$R^{10}$ represents H or $CH_3$;
q is an integer from 1 to 20;
glyceryl ester derivatives, represented by formula (IV):

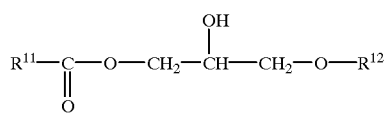
(IV)

in which:
$R^{11}$ represents a $C_8$–$C_{20}$ alkyl group; and
$R^{12}$ represents H or

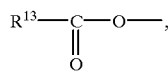

$R^{13}$ representing a $C_8$–$C_{20}$ alkyl group;
carboxylic amide derivatives, represented by formula (V):

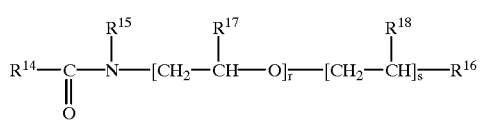
(V)

in which:
$R^{14}$ represents a $C_8$–$C_{20}$ alkyl group;
$R^{15}$ represents H or

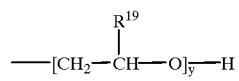

with $R^{19}$ representing H or $CH_3$ and y being an integer from 1 to 5;

$R^{16}$ represents H or

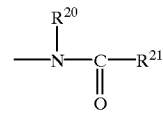

in which $R^{20}$ represents H or

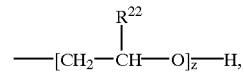

with $R^{22}$ representing H or $CH_3$ and z is an integer from 1 to 5, and $R^{21}$ is a $C_8$–$C_{20}$ alkyl;
$R^{17}$ and $R^{18}$ each independently represent H or $CH_3$;
r being equal to 0 or being an integer from 1 to 20; and
s being equal to 0 or 1.

16. A process according to claim 15, wherein the at least one hydrazine-type amino compound(s) is (are) added in a proportion of 10–10,000 ppm relative to the medium containing the acrylic acid to be purified.

17. A process according to claim 15, wherein the at least one hydrazine-type amino compound(s) is (are) added in an amount such that the molar ratio: hydrazine-type compound (s)/sum of the aldehydes present in the feed, is 0.5/1–10/1.

18. A process according to claim 15, wherein the distillation is carried out in two successive steps:
a first step, in a first distillation column for removal of a head fraction, fed with a flow of the medium containing the acrylic acid to be purified and receiving the at least one hydrazine-type amino compound, in order to remove, at the head of the first distillation column, light impurities and water generated during the reaction of the at least one hydrazine-type amino compound with the aldehyde impurities; and
a second step, in a second distillation column, fed with the flow from the foot of the said first distillation column, in order to effect, at the top of the second distillation column, the distillation of purified acrylic acid, and, at the foot of the second column, the removal of the heavy compounds comprising the products of reaction of the aldehyde impurities with the at least one hydrazine-type amino compound, the at least one polymerization inhibitor and the at least one nonionic surfactant;
the at least one polymerization inhibitor being added to the top of the first distillation column and to the top of the second distillation column, and optionally into the feed of these two columns, the nonionic surfactant(s) compound(s) being added, alone or as mixtures, into the feed of the column first and/or into the top of the first and second columns.

19. The process according to claim 15, wherein the at least one nonionic surfactant is added in a proportion of 10–1000 ppm relative to the medium containing the acrylic acid to be purified.

20. The process according to claim 15, wherein the at least one hydrazine-type amino compound(s) is (are) added in an amount such that the molar ratio: hydrazine-type compound (s)/sum of the aldehydes present in the feed is 1/1–5/1.

21. The process according to claim 15, wherein the at least one hydrazine-type amino compound is cyclohexylhydrazine or hexadecylhydrazine.

22. A process according to claim 15, wherein the at least one nonionic surfactant is (are) sent into a flow containing the acrylic acid, alone or in solution or suspension in a solvent, or in solution in a medium containing acrylic acid.

23. The process according to claim 15, wherein the at least one nonionic surfactant is (are) added in a proportion of 10–10,000 ppm relative to the medium containing the acrylic acid to be purified.

24. A process according to claim 15, wherein the at least polymerization inhibitor is selected from the group consisting of phenolic derivatives, phenothiazine and its derivatives, metal thiocarbamates, compounds containing nitroso groups, quinones (and) para-phenylenediamine derivatives represented by the general formula (VI):

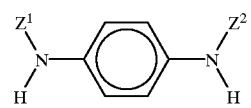

(VI)

in which $Z^1$ and $Z^2$ each independently represent an alkyl, aryl, alkylaryl or arylalkyl radical.

25. A process according to claim 15, carried out in a batchwise mode, or alternatively in a continuous mode.

26. A process according to claim 15, wherein the at least one nonionic surfactant is a cellulose ether.

27. A process according to claim 15, wherein said at least one nonionic surfactant is a methyl hydroxypropyl cellulose or a methyl hydroxyethyl cellulose.

* * * * *